United States Patent [19]
Koester

[11] Patent Number: 4,753,526
[45] Date of Patent: Jun. 28, 1988

[54] OPHTHALMIC IMAGE STABILIZATION SYSTEM

[75] Inventor: Charles J. Koester, Glen Rock, N.J.

[73] Assignee: The Trustees of Columbia University in the City of New York, New York, N.Y.

[21] Appl. No.: 590,414

[22] Filed: Mar. 16, 1984

[51] Int. Cl.$^4$ .......................... A61B 3/00; G02C 7/04
[52] U.S. Cl. .................................. 351/219; 351/160 R
[58] Field of Search ........................... 351/219, 160 R

[56] References Cited

U.S. PATENT DOCUMENTS

| | | |
|---|---|---|
| 2,430,851 | 11/1947 | Allen .............................. 351/219 X |
| 3,630,602 | 12/1971 | Herbert . |
| 3,820,879 | 6/1974 | Frisen . |
| 3,954,329 | 5/1976 | Pomerantzeff . |
| 4,056,310 | 11/1977 | Shimizu et al. . |
| 4,065,208 | 12/1977 | Currey . |
| 4,067,646 | 1/1978 | Nohda . |
| 4,134,647 | 1/1979 | Ramos-Caldera . |
| 4,378,147 | 3/1983 | Fujita . |

OTHER PUBLICATIONS

SU 148,200, published Oct. 26, 1960.
Ditchburn, et al., Vision With a Stabilized Retinal Image, Nature, vol. 170, No. 4314, Jul. 5, 1952, pp. 36, 37.
Yarbus, A. L., Eye Movements and Vision, 1967, pp. 35-38, 142-143.
Ratliff, The Role of Physiological Nystagmus in Monocular Acuity, Journal of Experimental Psychology, vol. 43, No. 3, Mar. 1952, pp. 163-172.
Riggs, et al., The Disappearance Of Steadily Fixated Visual Test Objects, Journal of the Optical Society of America, vol. 43, No. 6, Jun. 1953.
Koenderink, J. J., Contrast Enhancement and the Negative Afterimage Journal of the Optical Society of America, vol. 62, No. 5, May 1972.
Koenderink, et al., Method of Stabilizing the Retinal Image, Applied Optics, vol. 13, No. 4, Apr. 1974.

Primary Examiner—Rodney B. Bovernick
Attorney, Agent, or Firm—John P. White

[57] ABSTRACT

Disclosed are a system and a method for stabilizing the image of an object when the motions of that object are small, the motions are either rotatory or straight-line, and the object can be contacted. In the case of the eye a contact element structure contacts the eye and moves with the small rotational movements of the eye. The contact element is mounted to rotate about a pivot point which is outside the eye. The device forms a virtual image of a portion of the eye; this image is stabilized in that the virtual image does not move laterally with the small eye movements. The examining instrument, e.g., a biomicroscope, is focused on the virtual image. In laser treatment of the retina or other regions of the eye the laser beam can be directed through the system to the stabilized image.

31 Claims, 4 Drawing Sheets

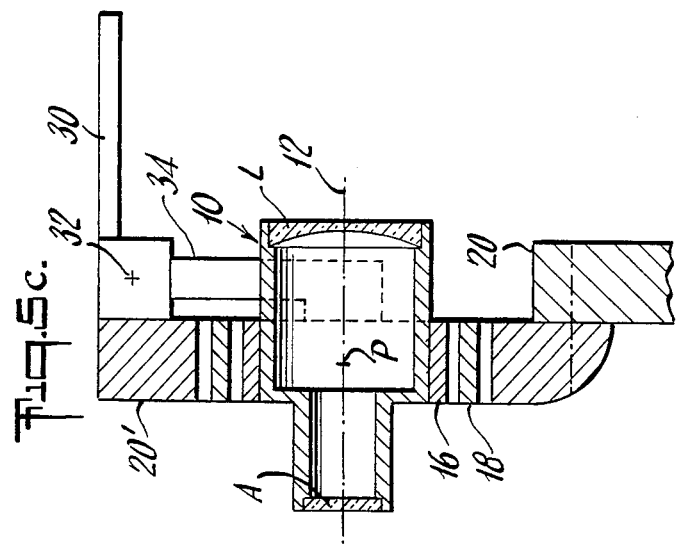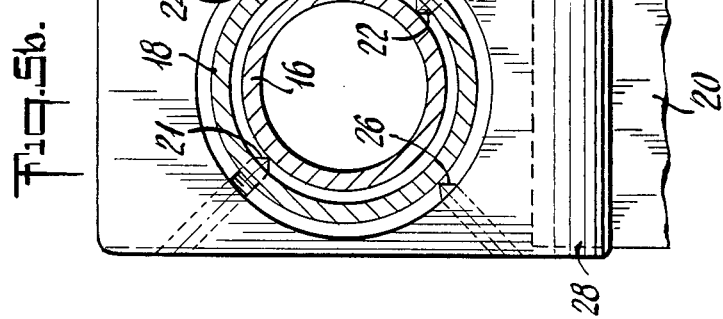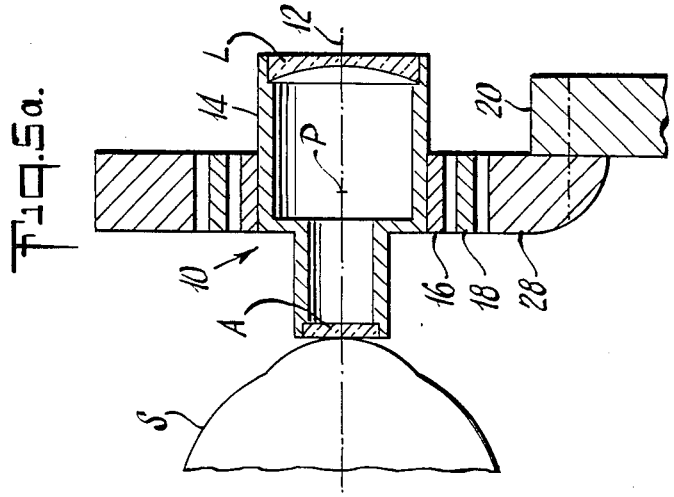

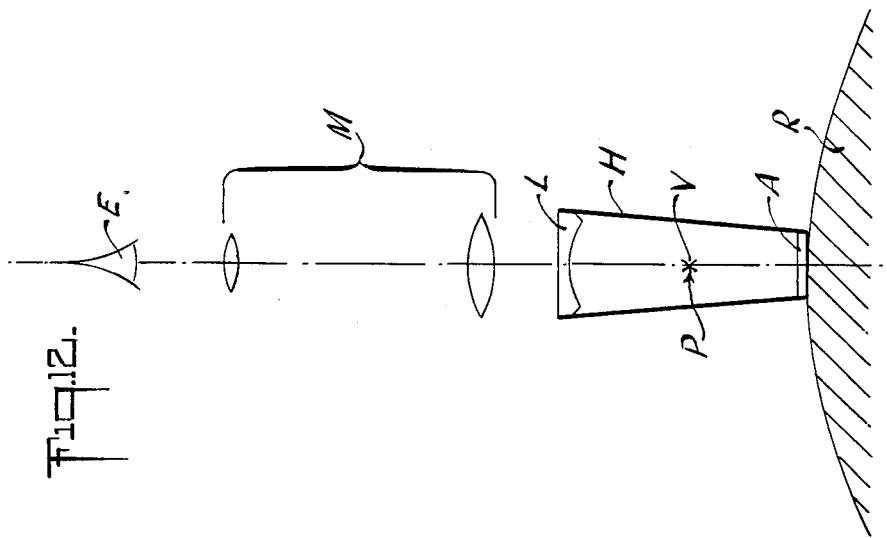
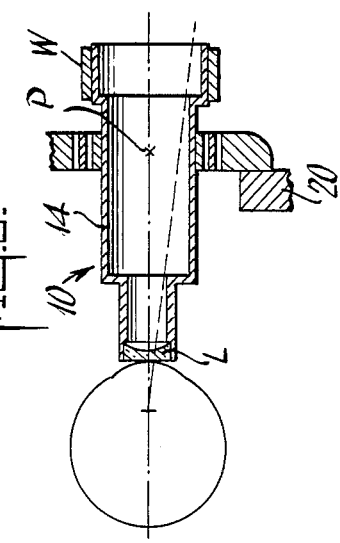
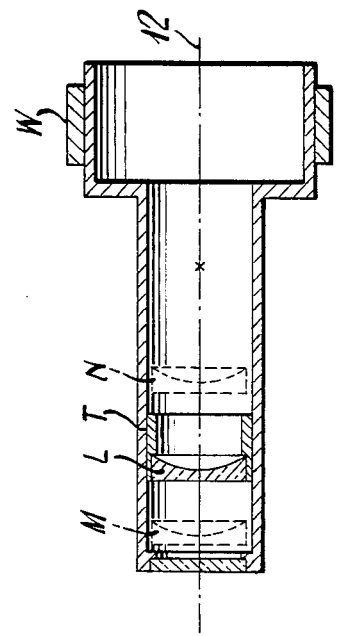

OPHTHALMIC IMAGE STABILIZATION SYSTEM

BACKGROUND AND SUMMARY OF THE INVENTION

The invention relates to techniques for examining objects that are subject to small movements which interfere with the examination process, particularly when magnification is used. For example, when structures within the eye are examined at high magnification, the limiting factor often is the rapid, involuntary motion of the eye. Not only do such small eye movements interfere with detailed examination, they also frustrate the accurate focusing of magnification devices, such as a specular microscope and, therefore, make flash photography difficult. Furthermore, in treaments such as laser photocoagulation of the retina, and in laser treatments of the trabecular meshwork, eye movements can interfere with effective treatment.

A number of optical instruments such as ophthalmoscopes, biomicroscopes, or specular microscopes are used for examination of detail within the eye. For low magnification applications, such as the indirect ophthalmoscope, small eye movements, of the kind which are involuntary and cannot be controlled even by a cooperative patient, tend to be of little consequence. However, for instruments with higher magnification, such eye movements become increasingly troublesome as the magnification is increased. These small, sudden eye movements often occur at the rate of about one per second. The excursion may be only a few minutes of arc, but this can cause severe blurring of an image of corneal cells, for example. Moreover, the changes in the cornea position with such movements tends to defocus the image of interest.

Various techniques have been proposed in the past for decreasng the motion of the eye, or reducing its deleterious effect on detailed examinations. For example, one method is to contact the cornea with a so-called dipping cone objective. The outermost element of such an objective has a flat, polished glass surface which, when in contact with the cornea with a slight pressure, substantially prevents motion of the cornea along the examination axis and inhibits, although it does not completely eliminate, rotational motion of the eye. This contact can be uncomfortable for the patient, and can cause slight abrasion and consequent adverse effect on the quality of the images which can be obtained. It is also common practice to use diagnostic contact lenses, which are generally hand-held in contact with the cornea and, as a result, do not move with the eye as it rotates. Their primary function has been to allow the fundus of the eye and certain other interior regions to be viewed at low magnification, e.g. through the biomicroscope. Such lenses may reduce the eye motion somewhat due to the contact with the eye and the inertia of the contact lens. However, when the eye moves, the image seen through such a lens still moves.

Another proposal has been to use a contact lens designed to move with the eye during its small, frequent rotation, and designed to form a virtual image of the plane of interest at the center of rotation of the eye. Because such a virtual image is located at the eye's center of rotation, the image will not translate either laterally or longitudinally as the eye rotates, so long as the contact lens moves with the eye. This virtual image is then reimaged by a stationary optical system for visual examination or photography. The plane of interest may be the endothelial or epithelial cell layers of the cornea, the epithelial cell layer of the lens, regions within the depth of the lens or the vitreous, or the retina. The optical power of the contact lens, along with its thickness, determine the depth within the eye of the plane which is imaged. This proposal is described in a prior U.S. patent application of the inventor herein, filed on Apr. 14, 1980 and now issued as U.S. Pat. No. 4,410,245, dated Oct. 18, 1983, hereby incorporated by reference. While this technique helps reduce the effect of involuntary eye movements, difficulties can arise in keeping the eyelids from interfering with the positioning of the contact lens on the eye. A mild suction can be applied to keep the contact lens firmly attached to the cornea, but this can introduce other complications. The system relies on the center of rotation of the eye, which may be at different locations in various patients, and which may have a slightly different location in a given eye, depending on the nature of the eye motion. Other difficulties can arise in that the optics of the contact lens, being fixed with respect to the patient's eye, may not remain cenetered with the optical system of the viewing device, due to patient movement.

In contrast with the known prior art proposals, this invention provides an apparatus and a method which stabilize the image of an object such as they eye, when the motions of that object are small, and when the object can be contacted. Exemplary apparatus embodying the invention includes a contact element structure comprising a contact element that contacts the eye and moves with the eye, and a lens that is fixed with respect to the contact element and forms a virtual image of a selected region of the eye. The contact element structure is supported to pivot freely about a point outside the eye, and the virtual image that it forms is stabilized in that it does not move laterally with said small eye movements. Of course the virtual image will, in general, rotate with the rotational motion of the image stabilizing system. But since the image is located at the center of rotation, the image has no lateral motion. The center of the image will have no longitudinal motion; points located away from the center of the virtual image will have a slight longitudinal motion either toward or away from the observer. When the rotational motions are small, these longitudinal motions will generally be negligible.

In one exemplary embodiment, best suited for examining the cornea, the stabilized virtual image is formed at the pivot point. When the eye moves, the contact element structure follows its motion by rotating about its pivot point, but the virtual image stays substantially stationary at the pivot point, and can be examined with an instrument such as a biomicroscope focused at the pivot point. Another exemplary embodiment is best suited for examining the fundus, and forms the stabilized virtual image at a region anterior to the center of rotation of the eye, and an examining instrument can be focused at that virtual image. The longitudinal position of the virtual image must be chosen so that it is stationary when the eye and the contact element move. In principle, the refractive error of the eye will determine the precise optical characteristics of the image stabilizing system necessary to produce a stationary image. It has been found that a lens having an adjustable position can achieve a stabilized image for a range of refractive errors.

Thus, one of the advantages of using the invention is that there is no need to place a contact lens on the eye. Another is that the center of rotation of the contact element structure is established by the invented apparatus rather than by the eye structure of the particular patient. Therefore, the virtual image is in a predetermined, stable position, and the optics remain centered with respect to the examining instrument. A further advantage is that in examining the fundus of patients with various refractive errors, image stabilization can be achieved by adjustment of the position of the lens. Numerous other advantages will become apparent from the remaining disclosure herein of illustrative embodiments of the invention.

BRIEF DESCRIPTION OF THE DRAWINGS

FIG. 5a is a partly sectional and partly elevational view of an exemplary eye examining system in accordance with the invention suitable for the cornea.

FIG. 5b is an elevational view showing the arrangement of gimbal rings and bearings.

FIG. 5c is similar to FIG. 5a, but with the addition of a centering key.

FIG. 6 is a sectional view of the contact element structure of an exemplary image stabilizing system suitable for the fundus.

FIG. 7 is a sectional view of the contact element of an exemplary image stabilizing system with an adjustable lens position, suitable for examining eyes with various degrees of refractive error.

FIG. 12 illustrates the application of the invention to examination of objects other than the eye. In studies on animals the motion of the tissue due to respiration and/or heartbeat can sometimes interfere with detailed observation or measurements.

DETAILED DESCRIPTION

Figure 1:
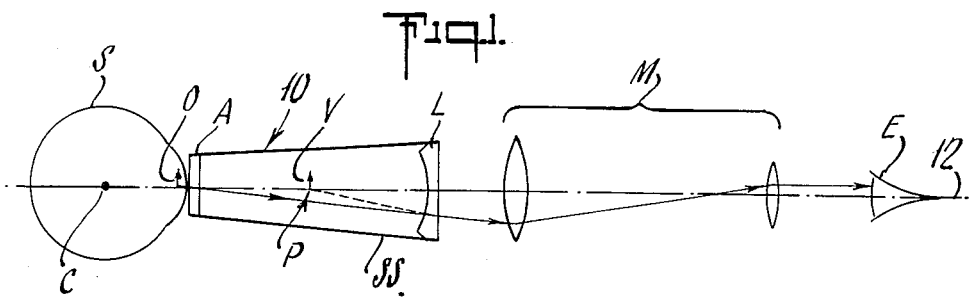
FIG. 1 illustrates schematically a nonlimiting example of utilizing the invention as an image stabiliation system for examining the cornea.
Figure 2:
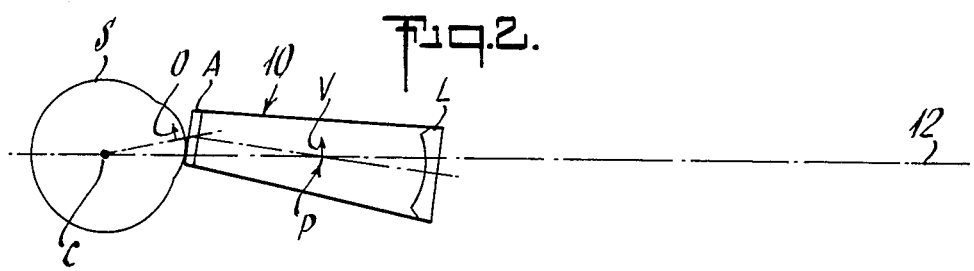
FIG. 2 shows a portion of the system shown in FIG. 1 and illustrates pivoting of a contact element structure with eye movement.

Referring to the schematic representation of FIGS. 1 and 2, a contact element structure generally indicated at 10 contacts a patient's eye and moves, with small eye movements, about pivot point P which is outside the eye, and forms a stabilized virtual image V of an object O. The virtual image remains substantially fixed with respect to the pivot point, and for practical purposes does not mvoe with movements of the imaged object O, such as the movement thereof illustrated in FIG. 2. A microscope schematically illustrated at M can therefore be focused on that virtual image, and object O can thus be reimaged for viewing by the observer's eye indicated at E. In this case the contact element structure 10 comprises a contact element A which is a flat glass plate that touches the eye and moves with it, a negative lens L positioned as illustrated, and a support structure sleeve SS which rigidly connects the contact element and lens to each other. The support structure sleeve is pivotally mounted on another support, not shown in FIGS. 1 and 2, which allows it to pivot freely about point P which is on the optical axis 12 and is intermediate contact element A and lens L. Referring to FIG. 2, when the patient's eye S is rotated as indicated about its center of rotation C, the contact element A has remained in contact with the cornea, and the contact element structure 10 has correspondingly rotated about pivot point P. Although the object O has moved as indicated, the virtual image V remains at the pivot point P, and microscope M can remain focused at that pivot point, thereby allowing a detailed and accurate examination of object O (e.g., the corneal epithelial or endothelial cell layer).

Figure 3:
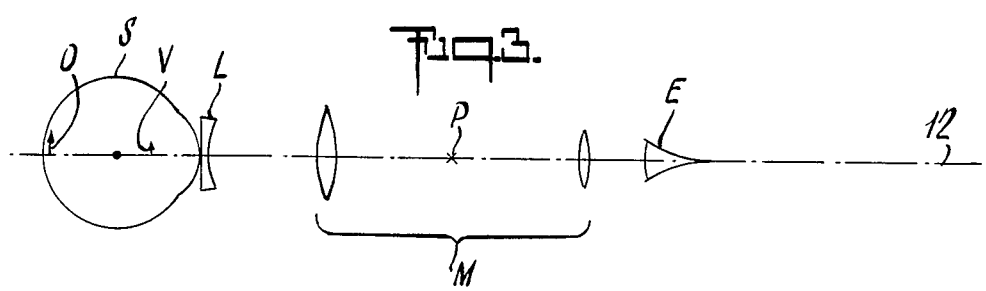
FIG. 3 illustrates another nonlimiting example embodying the invention—this time an image stabilizing system for the fundus.
Figure 4:
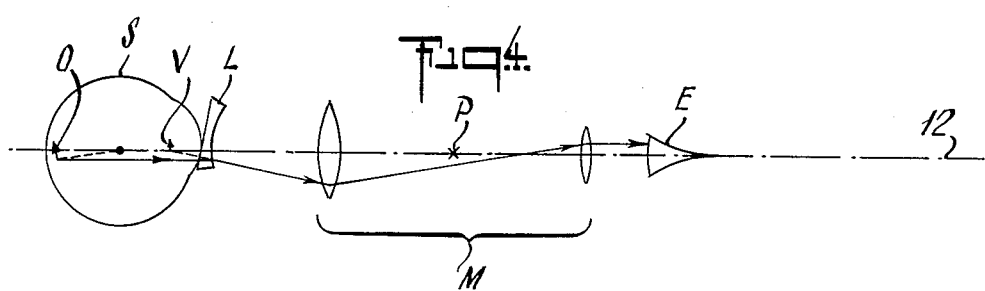
FIG. 4 illustrates pivoting of the contact element structure of FIG. 3 with eye movement.

In using an exemplary embodiment of the invention to examine the ocular fundus, as illustrated in FIGS. 3 and 4, the contact element and the lens can be combined into a single plano-concave lens L, which contacts the cornea as illustrated and is pivoted, by means not shown in FIGS. 3 and 4, about a pivot point P located some distance from the negative lens along the optical axis 12. In this case the position of the virtual image V of object O is in the eye and anterior to the center of rotation of the eye. Also in this case the pivot point is shown to be located within the stationary microscope viewing system, M. The precise location of the pivot point and the required power of the negative lens can be calculated by the method described below.

A particular and nonlimiting example of apparatus using the invention for cornea examinations is illustrated in FIGS. 5a–c, where components corresponding to what is shown in FIGS. 1 and 2 are identified by corresponding reference numerals or letters. In FIGS. 5a–c, contact element structure 10 again includes a contact element A and lens L but, instead of the conical sleeve SS shown in FIG. 1, they are rigidly connected to each other by means of a step-down sleeve 14 serving the same function. Step-down sleeve 14 can be adjusted longitudinally (along axis 12) by sliding it within ring 16. This adjustment serves to locate the pivot point at the optimum position. In order to allow contact element structure 10 to pivot freely about point P with small eye movements, ring 16 is mounted in a gimbal bearing comprising rings 16 and 18, along with bearings 21, 22, 24, and 26. The gimbals permit free rotation about two orthogonal axes. For purposes of illustration cone bearings are shown in FIG. 5b. Support post 20 remains stationary during an examination. A stationary microscope can be supported at a position stationary with respect to support post 20, and along the same optical axis 12 which passes through pivot point P, and can be used to examine the stationary image.

Illustrated in FIG. 5c is a centering key 30, supported on an extension 20' of stationary post 20 to pivot about a horizontal axis 32. Centering key 30 includes a downwardly projecting portion 34 which moves forwardly when the horizontal portion of the centering key is pushed down, and engages contact element structure 10 to center it along optical axis 12. When the horizontal portion of the centering key is then moved up, either manually or by means of a spring bias (not shown), contact element structure 10 is again free to pivot about point P.

In operation, the centering key is pushed down to center the contact element 10 on the optical axis, and contact element A and the patient's eye are brought into contact as illustrated. While the centering key is depressed, the microscope, together with the image stabilizing system, may be adjusted in position so as to bring details of interest into the field of the microscope. When this has been accomplished the centering key may be released to allow the contact element structure 10 to pivot freely. The stabilized virtual image of the selected corneal layer is then viewed through a microscope, or a similar instrument focused at pivot point P.

An exemplary contact element structure for use in fundus examination is illustrated in FIG. 6, where again elements corresponding to those shown in FIGS. 3 and 4 are identified by the same reference numerals or letters. In FIG. 6, contact element 10 comprises a plano-concave lens L at the smaller end of a step-down sleeve 14. The contact element structure shown at FIG. 6 is supported for pivoting about point P by a gimbal arrangement which is not shown expressly in FIG. 6 but matches both in structure and function that illustrated in detail in FIGS. 5a–c, and uses a corresponding centering key and a corresponding microscope or similar instrument. A counterweight ring is illustrated at W.

An exemplary contact element structure for use with eyes having various refractive errors is illustrated in FIG. 7. The plano-concave lens L is mounted in a sleeve T that can be adjusted in longitudinal position (along axis 12). In position L the lens is located so as to form a stabilized image of the fundus of a patient with no refractive error. In position M the lens forms a stabilized fundus image of a myopic patient, and in position N the lens forms a stabilized fundus image of a hyperopic patient, e.g., an aphakic patient. A counterweight, W, is adjustable in longitudinal position (along axis 12) to maintain balance for various positions of the lens.

Figure 8:
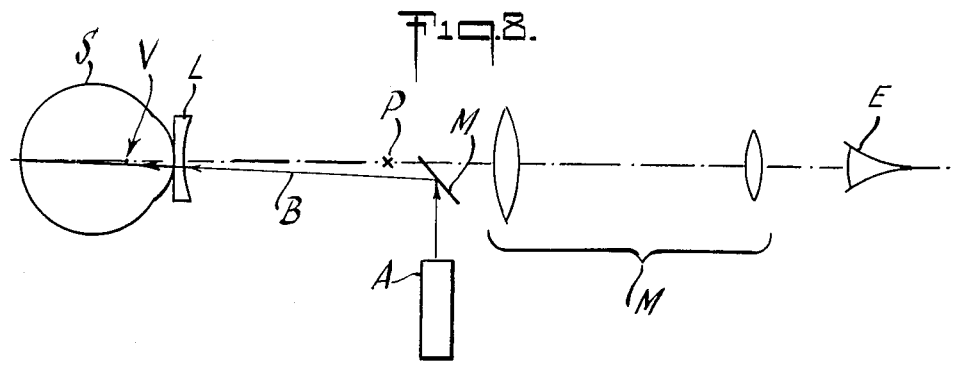
FIG. 8 illustrates a nonlimiting embodiment of the invention in which a laser beam is directed through the image stabilizing system to a region within the eye, while at the same time permitting the examiner to monitor the location of the laser beam in the eye.
Figure 9:
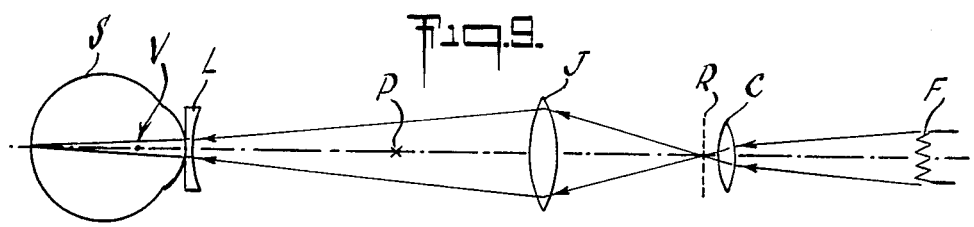
FIG. 9 illustrates another example of the invention in which an image is presented to the eye of an observer through the optical system of the invention so that the image is stabilized with respect to the retina of the observer.

FIGS. 8 and 9 illustrate how the invention can be used in reverse, that is, to send light into the eye in such a way that it travels to the same point in the eye regardless of small eye movements. In the example shown in FIG. 8 a laser shown at A generates a light beam, B, that is directed by mirror M into the image stabilizing system. The image stabilizing system in this case comprises lens L mounted as earlier described so that it contacts the cornea of eye S, and so that it pivots about point P. In this example, the laser bearm is directed by mirror M toward the virtual image V of the fundus. This assures that beam location on the fundus will be stabilized. The actual path of the beam after passing through the lens L is shown by the solid line. M represents a microscope such as the biomicroscope, used by the observer E to examine the eye S and to monitor the position of the laser beam on the fundus.

A principal application of the example in FIG. 8 is laser photocoagulation of the retina, for treatment of detached retinas, diabetic retinopathy, macular degeneration and certain other conditions. However, laser beams may be directed into the eye for diagnostic purposes as well. Laser Doppler velocimetry is a recently developed technique that measures blood cell velocity in selected retinal vessels. It requires that a low power laser beam be directed at a specific retinal vessel and remain at a fixed position on that vessel long enough to detect the light scattered back to detectors. Eye movement is a critical limitation on the technique. It is believed that this invention can ease the problem of directing the laser beam to a specific blood vessel and maintaining its position on the vessel.

FIG. 9 illustrates use of the invention to project a stabilized light pattern or image on the retina of the subject's eye, S. Light from a source, F, is collected by a condenser lens C, and illuminates a target or reticle denoted by R. Light from this target is directed by objective lens J to a focus at the virtual image of the retina at V. As in the previous example, the image stabilizing system comprises the lens L mounted as earlier described so that it contacts the eye S and pivots at point P. Since the retinal image at V is stabilized by the action of the image stabilizing system, the pattern of light from the target will be stabilized on the retina.

Figure 10:
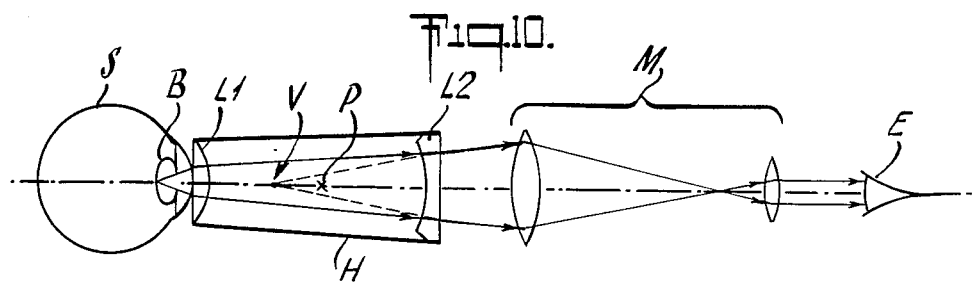
FIG. 10 is an illustration of an embodiment of the invention in which the image of the posterior capsule of the eye lens is stabilized.

FIG. 10 illustrates the use of one form of the invention for examination of another region within the eye, the posterior capsule, B, of the lens. In cataract surgery, one technique is to remove the cataractous lens material while leaving the posterior portion of the capsule in place. A possible complication of this technique is the later opacification of this capsular membrane. It is believed that this invention can help both in the examination related to this condition and in the laser treatment.

The system in this case comprises positive lens L1 contacting the cornea, negative lens L2, and housing H that fixedly connects these two optical elements and that pivots about point P. Letter I designates the iris of the eye. M is the microscope used by observer E to examine the stabilized image, which in this case, appears at virtual image V, anterior to the cornea.

Figure 11:
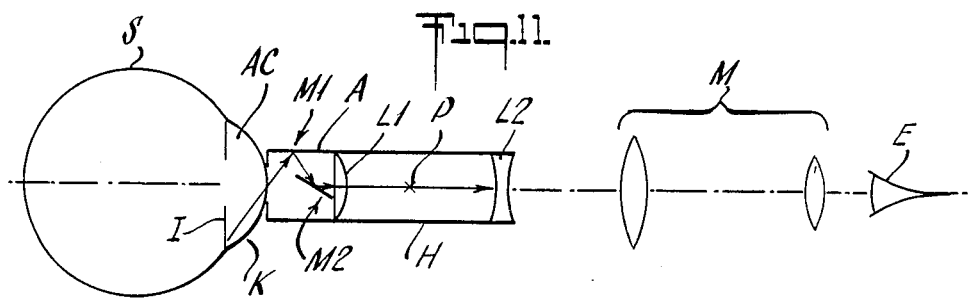
FIG. 11 illustrates the use of the invention for stabilizing the image of the angle of the anterior chamber of the eye.

FIG. 11 illustrates the use of the invention for examination of the angle of anterior chamber (AC) of the eye. The angle is, generally speaking, the narrow region between the peripheral cornea, K, and the iris, I, and includes the trabecular meshwork, the structure through which aqueous humor flows in order to exit from the eye. The image stabilizing system in this case comprises contact element A, which contains mirrors M1 and M2, and attached to which is positive lens L1, also negative lens L2, and the housing H that holds the previously mentioned elements and that pivots about point P. Microscope M is used by observer E to examine the virtual image.

In both FIGS. 10 and 11 a laser can be combined with the image stabilizing system, in the manner described in connection with FIG. 8, for purposes of laser treatment.

In order that the contact element move precisely with the eye as the eye undergoes its small rotational motions, the contact element should be pressed against the cornea with a sufficient but not excessive force. Such a force can be provided by the operator as he moves the instrument, including the contact element, into contact with the eye. A preferred method is to mount the contact element and the gimbal arrangement on a spring loaded linear bearing (not shown). When the contact element is placed against the cornea, the spring tension will determine the force on the cornea; this can be pre-adjusted to an appropriate level, strong enough to assure accurate tracking of the contact element with the cornea, but not so strong as to cause indentation of the cornea or other adverse effects to the cornea.

FIG. 12 illustrates the use of the image stabilizing system with a specimen R that is vibrating or otherwise moving through small excursions in directions perpendicular to the axis X. An example would be the ear or other structure on the surface of an animal, where respiration and heart pulse will cause motion of the structure being examined. The contact element A, shown as a thin transparent member, contacts the specimen and moves with it when the specimen translates. Motion of the specimen in the direction of axis X is prevented by the contact element. The lens L and the contact element A are moutned in a housing H, which is free to pivot at point P. Observer E views the spcimen through microscope M. focused on the virtual image of the specimen at V, generally located at the pivot point P. The contact element A may be omitted in cases where the specimen can be contacted by the housing.

The position of the pivot point and the required power of the lens are found as follows. For the examination of the cornea or other object plane very close to the contact element the procedure is straightforward. The location of the pivot point is chosen to be at a convenient distance from the eye, typically 20 to 50 mm. The power of the negative lens is then selected so that the virtual image is formed at the pivot point. This virtual image will then be stationary and can be viewed through a stationary biomicroscope or other examining instrument.

For the examination of the fundus the calculation is more involved. First, the object (the fundus) is moving with a different velocity and direction than the contact element. Second, as the cornea and the contact element each rotate about their respective centers of rotation, an effective prism is formed. For example, if the cornea and contact element touch at just one point, then the tear layer between the two surfaces forms a prism. The angle of the prism increases as the rotational motion of the eye increases. As in the previous design, the first step is to select a convenient pivot position relative to the eye. With the eye and the image stabilizing system rotated slightly from their original, aligned positions, a ray is traced from the posterior pole of the fundus, passing through the center of rotation of the eye, through the prism formed at the cornea/contact element interface, and through the optics of the image stabilizing system. When this ray emerges from the image stabilizing system, it is extended backwards toward the fundus until it crosses the axis. The optics of the image stabilizing system are selected so that the virtual image is formed at the intersection point. When this is accomplished the virtual image of the posterior pole will be stationary.

Other regions within the eye can be examined using image stabilizing systems designed specifically for those regions, for example by combining known optical systems such as the Goldmann gonioprism with the image stabilizing principles described herein.

While examination of the eye has been used as the example in describing the operation of the image stabilizing system, the system works equally well in reverse. That is, a beam or pattern of light can be projected through the image stabilizing system, and that beam or pattern will be stationary with respect to the selected region of the eye. In laser photocoagulation of the retina, for example, if the beam is focused to a point immediately adjacent to a retinal blood vessel, the beam will remain focused at that point on the retina even if the eye undergoes a small rotational motion. Other laser treatments requiring high accuracy in positioning the laser beam include: photocoagulation in and near the macula, laser trabeculoplasty, and neodymium YAG laser capsulotomy and membranotomy.

Other diagnostic procedures involve sending low energy laser beams into the eye. Laser doppler velocimetry and laser ophthalmoscopy both require precise localization of the laser beam on the retina. The image stabilizing system offers a relatively inexpensive, easily applied method for neutralizing the effect of small eye rotations.

A final but nonlimiting example of the image stabilizing system used in reverse is the presentation of stabilized images onto the retina of an observer, to test the response of the observer to such an image. Such tests have been performed in well known psychophysical experiments to demonstrate the fading of an image that is stabilized on the observer's retina. Special contact lenses have been used in these experiments. The image stabilizing system presents the opportunity to perform such tests without the fitting of special contact lenses. Additionally, clinical tests can be devised to test vision under precisely controlled conditions. Visual acuity of pre-selected regions of the retina may be determined. In some cases, it can be useful to identify visual field defects using the image stabilizing system. Many patients experience difficulty in maintaining fixation, i.e. their direction of gaze, during such testing. The image stabilizing system neutralizes the effects of small eye motions so that they do not affect the locating and plotting of visual field defects. This can be of value in the plotting of field defects at or near the macula.

Some ophthalmic measurement systems, such as the applanation tonometer for determining intra-ocular pressure, utilize a split image viewing device to permit measurements to be made in spite of eye movements. The image stabilizing system offers an alternative approach: stabilization of the image of the applanated area, so that the split image approach is not necessary.

Another application is the microscopic examination of the surface of objects that are vibrating in a linear fashion. For example, a component may need to be examined under conditions in which it vibrates along a straight line. The vibration could also be in a plane, e.g. a circular or elliptical motion of the object.

As in the case of the eye examination, the front element of the system contacts the object and moves with it. The system is mounted so as to pivot at some point at a pre-determined distance from the object. The power of the lens (or lenses) and the location of the pivot point are chosen so that the image of the surface is stabilized. That image can then be magnified and examined using a stationary optical systm of conventional design.

In this case the front element is designed so that it will move precisely with the object being examined. One technique is to provide a compliant material with a high coefficient of friction to contact the vibrating object. A rubber gasket material, or an "O Ring" will be suitable in cases of small amplitude vibration.

The optical system comprises a negative lens positioned so that the image of the object under study is located at the pivot point. A viewing device in the form of a long working distance microscope can then be used to examine the virtual image.

I claim:

1. A system for forming a stabilized virtual image of a region of a patient's eye comprising a support and a contact element structure which is supported by the support so as to move with small rotational eye movements transverse to an optical axis about a pivot point which is outside the eye and defined by the intersection of two axes orthogonal to the optical axis, the contact element structure comprises a negative objective lens and a transparent plate having a surface shaped so as to contact the cornea of the patient's eye and move with a rotational action against the cornea in response to the eye movements, the negative objective lens being positioned with respect to the transparent plate so as to form the stabilized virtual image wherein the image does not move with the eye movements.

2. A system as in claim 1 in which the stabilized virtual image is outside the eye.

3. A system as in claim 1 in which the stabilized virtual image is of the eye's cornea.

4. A system as in claim 1 in which the stabilized virtual image is at the pivot point.

5. A system as in claim 1 in which the surface of the transparent plate contacting the eye is flat and the negative objective lens is located proximal to the pivot point.

6. A system as in claim 1 further comprising an instrument focused at the stabilized virtual image for magnifying and viewing same.

7. A system as in claim 1, wherein the instrument is a microscope secured to remain fixed relative to said stabilized virtual image and focusable thereon to allow viewing a magnified image thereof.

8. A system as in claim 1 in which the stabilized virtual image is inside the eye.

9. A system as in claim 1 in which the stabilized image is of the eye's fundus.

10. A system as in claim 1 in which the stabilized image is of the posterior capsule of the eye lens.

11. A system as in claim 1 in which the stabilized image is of the narrow region between the peripheral cornea and the iris of the anterior chamber of the eye.

12. A system as in claim 1 in which the transparent plate and the negative objective lens are combined into a plano-concave lens whose flat surface contacts the cornea of the eye.

13. A system as in claim 12, of the region within the eye is the fundus.

14. A system as in claim 1 in which the contact element structure is gimballed relative to said support.

15. A system as in claim 14 including a gimbal arrangement mounted on said support for gimballing about said pivot point and means for securing the contact element structure to said gimbal arrangement.

16. A system as in claim 15 including means for locking the gimbal arrangement and with it the contact element structure, at a centered position relative to the support.

17. A system as in claim 1, wherein the contact element structure further comprises a positive objective lens.

18. A system as in claim 17, wherein the contact element structure further comprises a mirror.

19. A system as in claim 18, wherein the region of the eye is the narrow region between the peripheral cornea and the iris of the anterior chamber of the eye.

20. A system as in claim 1, wherein the position of the negative objective lens is adjustable with respect to the transparent plate.

21. A method of examining a region of a patient's eye which comprises contacting the eye with the system of claim 1 so as to form a stabilized virtual image of the region, and examining the stabilized virtual image.

22. A method as in claim 21 in which the stabilized virtual image is of the eye's fundus.

23. A method as in claim 21 in which the contact element structure is gimballed on the support to permit movement about said pivot point with said small rotational eye movements.

24. A system for forming a stabilized virtual image of a selected region of a patient's eye comprising a support, a contact element structure, which is supported by the support so as to move with small rotational eye movements transverse to an optical axis about a pivot point which is outside the eye and defined by the intersection of two axes orthogonal to the optical axis, and means for illuminating a selected region of the eye with a light beam which passes through the contact element structure and continues to strike the selected region despite said eye movements, the contact element structure comprises a negative objective lens and a transparent plate having a surface shaped so as to contact the cornea of the patient's eye and move with a rotational action against the cornea in response to the eye movements, the negative objective lens being posiitioned with respect to the transparent plate so as to form the stabilized virtual image wherein the image does not move with the eye movements.

25. A system as in claim 24 in which the light beam comprises a laser beam for photocoagulation of the eye's retina.

26. A system as in claim 24, in which the light beam comprises a low power, diagnostic laser beam.

27. A system as in claim 24 in which the light beam comprises a selected light pattern for illuminating the eye's retina in a selected pattern of lighter and darker areas which does not move relative to the retina with small eye movements relative to the support.

28. A system as in claim 24 including means for concurrently viewing said stabilized virtual image.

29. A system as in claim 24 in which the transparent plate and the negative objective lens are combined into a plano-concave lens whose flat surface contacts the cornea of the eye.

30. A system for forming a stabilized virtual image of a selected region of an object, despite small movements of the object in directions transverse to an optical axis, comprising a support and contact element structure which is supported by the support so as to move with the small movements of the object about a point which is outside the object and is defined by the intersection of two axes orthogonal to the optical axis, the contact element structure comprises a negative objective lens and a transparent plate having a surface shaped so as to contact the surface of the object and move with a rotational action against the surface of the object in response to the small movements, the negative objective lens being positioned with respect to the transparent plate so as to form the stabilized virtual image.

31. A method of examining a selected region of an object which comprises contacting the object with the system of claim 30 so as to form a stabilized virtual image of the selected region of the object, and examining the stabilized virtual image.

* * * * *